(12) United States Patent
Brown

(10) Patent No.: US 6,363,949 B1
(45) Date of Patent: Apr. 2, 2002

(54) DENTAL CARE DEVICE

(76) Inventor: Thomas W. Brown, 1421 Lachateau, Liberty, MO (US) 64068

( * ) Notice: Subject to any disclaimer, the term of this patent is extended or adjusted under 35 U.S.C. 154(b) by 0 days.

(21) Appl. No.: 09/685,108

(22) Filed: Oct. 10, 2000

(51) Int. Cl.⁷ .............................................. A61C 15/00
(52) U.S. Cl. ........................ 132/325; 132/326; 132/324; 132/327
(58) Field of Search ................................ 132/322, 323, 132/324, 325, 326, 327, 328; 601/141; 606/161

(56) References Cited

U.S. PATENT DOCUMENTS

| | | | |
|---|---|---|---|
| 4,178,947 A | 12/1979 | McCourry et al. | |
| 4,214,598 A | 7/1980 | Lee | |
| 4,455,704 A * | 6/1984 | Williams | 132/325 |
| 4,574,823 A | 3/1986 | Uriss | |
| D303,426 S | 9/1989 | Simonian | |
| 5,269,331 A * | 12/1993 | Tanriverdi | 132/325 |
| 5,375,615 A * | 12/1994 | Wahlstrom | 132/325 |
| 5,438,726 A * | 8/1995 | Leite | 132/325 |
| 5,560,378 A * | 10/1996 | Tiphonnet | 132/325 |
| 6,056,763 A * | 5/2000 | Parsons | 606/161 |
| 6,092,536 A * | 7/2000 | Owens | 132/325 |

\* cited by examiner

Primary Examiner—Pedro Philogene
(74) Attorney, Agent, or Firm—Shughart Thomson & Kilroy P.C.

(57) ABSTRACT

A dental care device combines a flossing tool for dispensing dental floss and holding a length of the floss under tension with a double-edged tongue scraper. The dental care device includes an ergonomic handle. A floss fork is connected to one end of the handle and includes a pair of prongs extending outwardly from the handle, the prongs each having tips adapted to support a length of dental floss across the gap between the prongs. The device includes a floss tensioner having a floss cog rotatably mounted in the handle. The handle includes a tool storage compartment which may be used to contain dental hygiene tools such as a microbrush and a pick. The tongue scraper is attached to the end of the handle opposite the floss fork and includes a semicircular blade having opposing edges which are formed so that one of the edges is sharper than the other.

25 Claims, 3 Drawing Sheets

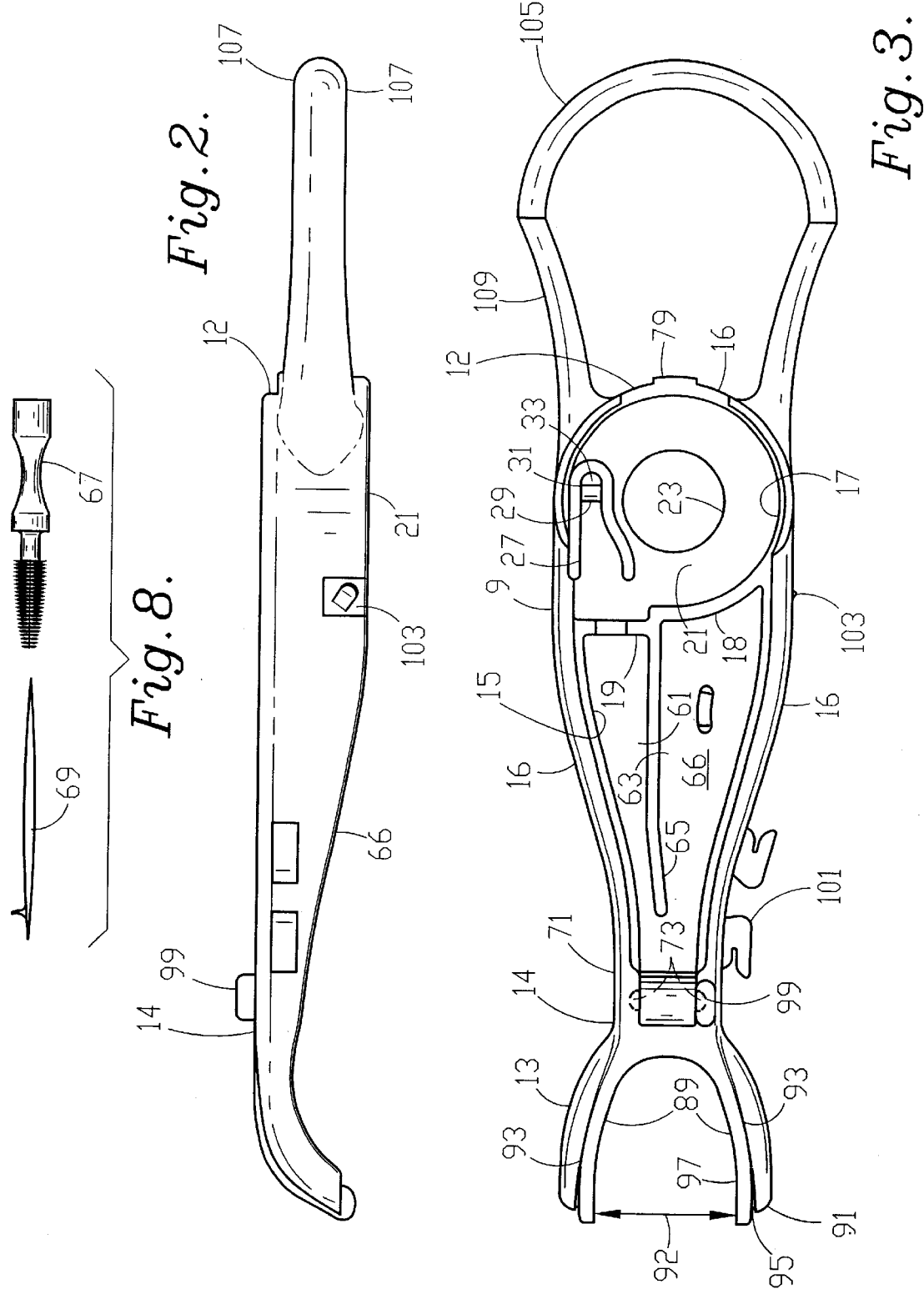

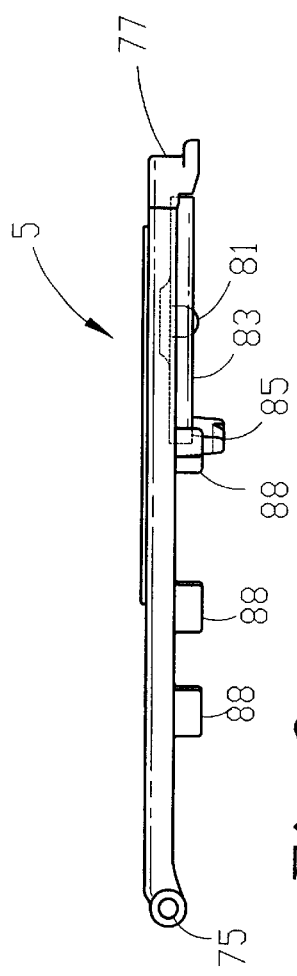
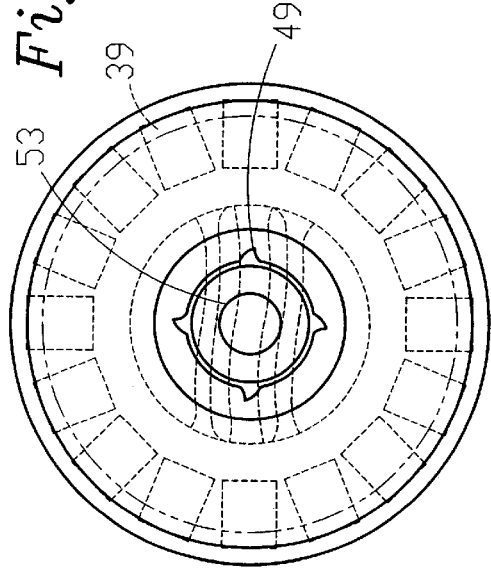
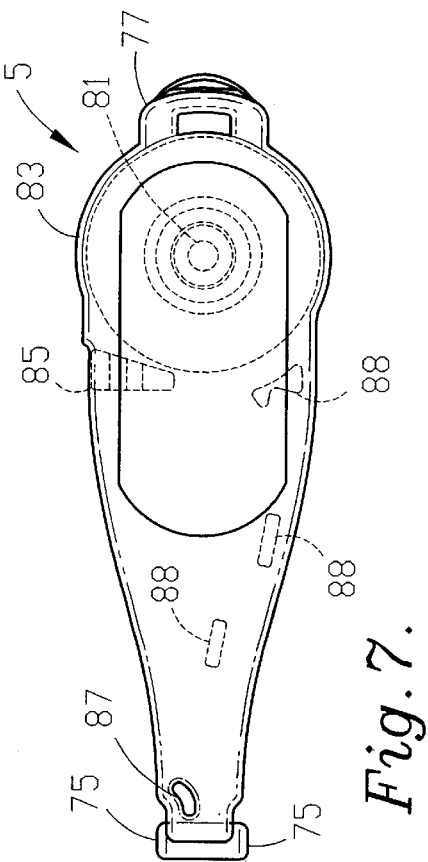
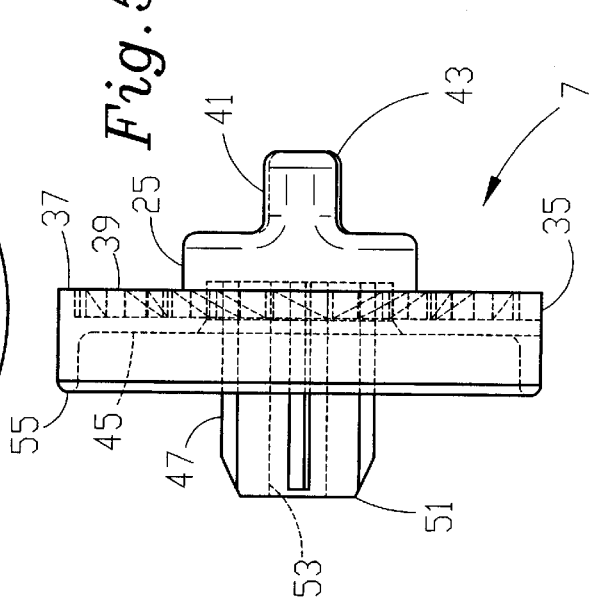

DENTAL CARE DEVICE

BACKGROUND OF THE INVENTION

1. Field of the Invention

The invention relates generally to the field of dental care devices, and more particularly to a dental floss applicator having a floss tensioner combined with a tongue scraper.

2. Description of the Related Art

Good oral hygiene requires daily flossing to clean areas between teeth that cannot be reached by brushing alone. Loose strands of dental floss can be used to accomplish this task, however this method can tend to be somewhat messy and gaps between back teeth can be hard to reach. Dental floss applicators can be used to improve the flossing process. Floss applicators are well known in the art and generally provide a handle with a piece of dental floss held under tension between the prongs of a fork proximate one end of the handle. Use of a floss applicator allows the user to floss without having to insert his or her hands into the mouth and makes it easy to reach back teeth.

Floss applicators may be of a single-use, disposable variety, or they may be reusable. One well known reusable applicator is the PHB Model P03H flosser manufactured by PHB Inc. of Osseo, Wis. This floss applicator is manufactured of polypropylene and includes a handle with a pair of floss supporting prongs spaced along the longitudinal centerline of the handle at one end and a floss tensioning mechanism at the other. This design has several disadvantages. First, the spacing of the floss prongs along the longitudinal centerline of the flosser makes it difficult to floss between the back teeth, as the corner of the user's mouth interferes with the handle of the flosser. Second, the polypropylene material used in the construction of the flosser is not durable or heat resistant. The flosser is therefore easily broken and not autoclavable or dishwasher safe. Third, the PHB flosser and other currently available flossing tools come equipped with acrylic yarn floss which shreds easily when subjected to the repeated use of a short section of floss that occurs when using a flossing tool.

In recent years, the advantages of using a tongue scraper have become more widely known. Cleaning the tongue with a tongue scraper helps eliminate bacteria that cause bad breath and plaque. Regular tongue scraping can reduce oral bacteria by up to 400% versus normal brushing. A wide variety of tongue scrapers are available on the market. U.S. Pat. No. Des. 303,426 discloses a combined tongue scraper and dental flossing tool, however this device uses a single-edged tongue scraper blade and has no tensioning mechanism for the flossing tool. A double-edged tongue scraper blade is preferable to a single-edged blade because the two edges can be honed to different sharpnesses, allowing the user to clean his or her tongue in graduated steps, or to simply select an edge that meets the user's individual taste.

It is apparent that there remains a need for a dental care device that includes a flossing tool, which is durable and easy to use, in combination with a double edged tongue scraper. Heretofore there has not been a dental care device available with the advantages and features of the present invention.

SUMMARY OF THE INVENTION

The current invention is a dental care device which combines a flossing tool for dispensing dental floss and holding a length of the floss under tension with a double edged tongue scraper. The dental care device includes a body with a handle portion having opposing ends and including a cavity having a bottom wall and upstanding sidewalls. A lid is hingedly connected to the body and selectively covers the cavity.

A floss fork connected to one end of the handle portion includes a pair of prongs extending outwardly from the handle portion. The prongs each have tips which are adapted to support a length of dental floss across the gap between the prongs. The prongs are oriented such that the floss supported by the prongs runs perpendicular to the longitudinal axis of the handle.

The device includes a floss tensioner having a floss cog rotatably mounted in the cavity between the bottom wall and the lid. The floss cog has a ratchet wheel with a plurality of teeth and a spindle connected to said ratchet wheel which is adapted to retain a spool of dental floss. A ratchet pawl connected to the body selectively engages the ratchet wheel teeth, allowing the user to tighten the floss across the floss fork and selectively spool out a length of floss as needed.

The cavity of the handle portion includes a floss channel which extends from the floss tensioner to the floss fork and a tool storage compartment which is separated from the floss channel by a dividing wall. The tool storage compartment may be used to contain dental hygiene tools such as a microbrush and a pick which are used to remove food particles and plaque from proximal spaces and orthodontics.

The lid serves to retain the tools in the storage compartment as well as to retain the floss cog in position and to press the ratchet wheel against the pawl, causing the pawl to engage the ratchet wheel teeth. The lid is preferably transparent so that the user can see how much floss remains on the floss cog without opening the lid.

The tongue scraper is attached to the end of the handle portion opposite the floss fork and includes a semicircular blade having opposing edges. Each end of the blade is connected to the body by a mounting arm. The edges of the tongue scraper blade are formed so that one of the edges is sharper than the other.

The body and lid of the dental care device are molded of polycarbonate which is strong, durable, and heat resistant, making the device autoclavable and dishwasher safe.

OBJECTS AND ADVANTAGES OF THE INVENTION

The principal objects and advantages of the present invention include: providing a dental care device having a floss holder and a tongue scraper; providing such a device which is comfortable and easy to use; providing such a device which includes a floss tensioner which allows the user to accurately and easily control the tension on the floss; providing such a device which is autoclavable and dishwasher safe; providing such a device which includes a storage compartment for small dental hygiene tools; providing such a device wherein the tongue scraper includes a double-edged blade with the edges having different sharpnesses; providing such a device which is adapted for use with polytetrafluorethylene floss; and providing such a device which is economical to manufacture, capable of a long operating life and particularly well-adapted for the proposed usage thereof.

BRIEF DESCRIPTION OF THE DRAWINGS

FIG. 2 is a side view of the body of the dental care device.

FIG. 3 is a bottom view of the body of the dental care device.

FIG. 4 is a top view of the floss cog of the dental care device.

FIG. 5 is a side view of the floss cog of the dental care device.

FIG. 6 is a side view of the lid of the dental care device.

FIG. 7 is a top view of the lid of the dental care device.

FIG. 8 is a side view of a microbrush and pick set for use with the dental care device.

DETAILED DESCRIPTION OF THE PREFERRED EMBODIMENT

Figure 1:
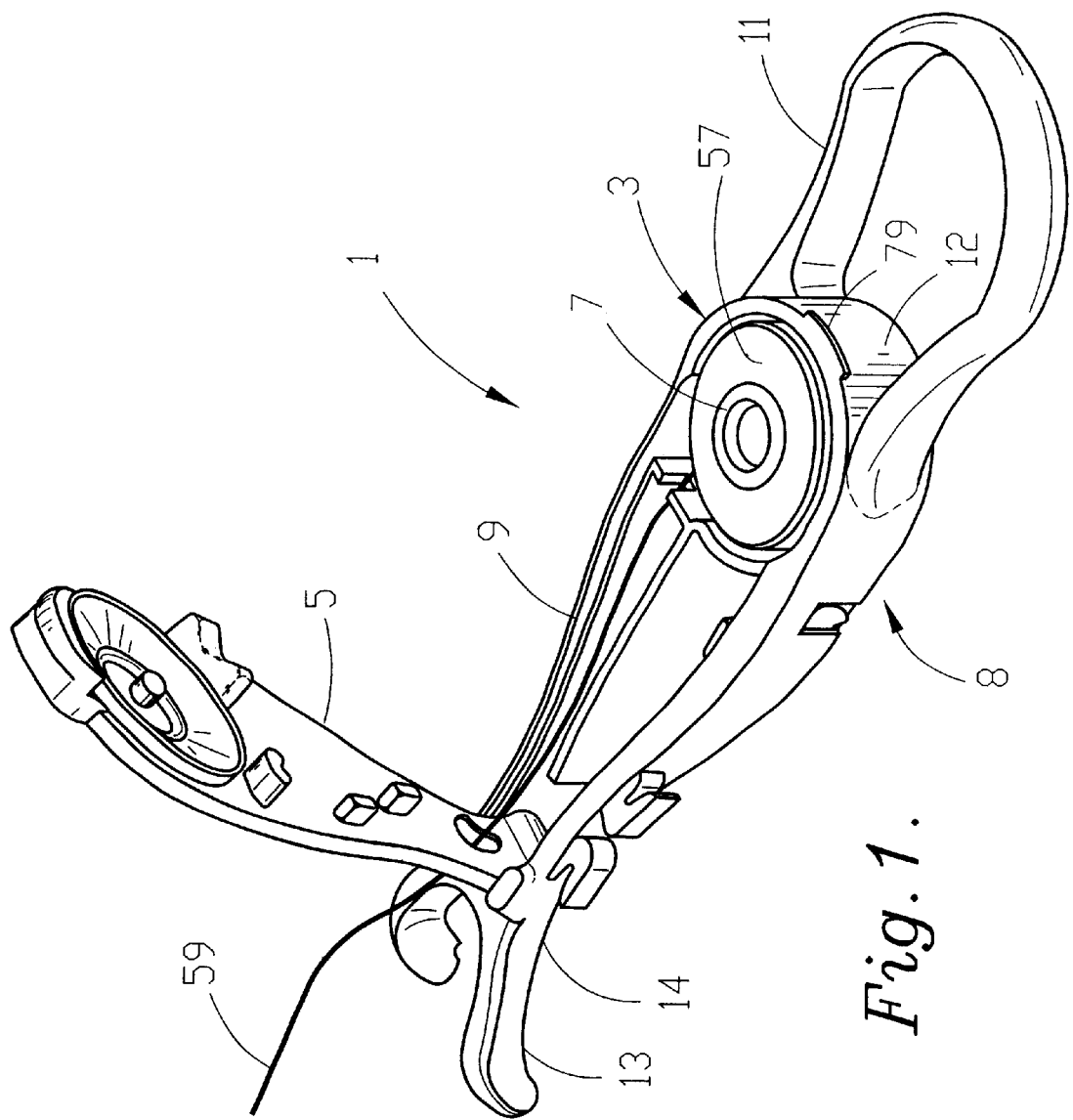
FIG. 1 is a perspective view of a dental care device embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the embodiment being described and designated parts thereof Said terminology will include the words specifically mentioned, derivatives thereof and words of a similar import.

Referring to the drawings in more detail, the reference number 1 generally designates a dental care device embodying the present invention. The dental care device 1 (FIG. 1) includes a body 3, a lid 5 and a floss cog 7. The body 3 (FIGS. 2 and 3) is molded of a strong, durable plastic which is preferably polycarbonate. Polycarbonate has the advantage of being heat resistant, the use of which makes the device 1 autoclavable and dishwasher safe. The body 3 includes a central handle portion 9, a tongue scraper 11 connected to a first end 12 of the handle portion 9, and a floss fork 13 connected to a second end 14 of the handle portion 9. The handle portion 9 is ergonomically designed so as to comfortably fit the hand of a user in either a tongue scraping or tooth flossing orientation.

The handle portion 9 contains a cavity 15 having upstanding sidewalls 16. The cavity 15 includes a generally cylindrical floss well 17 which is located proximate the first end 12 of the handle portion 9 and is sized to accept the floss cog 7, the combination of the cog 7 and floss well 17 forming a floss tensioner 8. The floss well 17 has a curved sidewall 18, a floss guide 19 connected to the sidewall 18, and a bottom wall 21. The bottom wall 21 has a central receiver 23 sized to receive a cylindrical arbor 25 of the floss cog 7. The bottom wall 21 also includes an integral ratchet pawl 27 oriented tangentially to the receiver 21. The pawl 27 has a generally triangular tooth 29 which extends into the floss well 17 and a release tab 31 which extends outwardly from the body 3 and includes a gripping surface 33.

The floss cog 7 (FIGS. 4 and 5) is molded of a strong, durable plastic material which is preferably nylon because nylon is somewhat self-lubricating and therefore provides for ease of movement of the cog 7. However, other materials such as polycarbonate could also be used. The floss cog 7 includes a ratchet wheel 35 having a first planar surface 37 with an annular row of teeth 39 which selectively engage the tooth 29 of the pawl 27 when the cog 7 is installed in the floss well 17 of the body 3. The arbor 25 extends from the first surface 37 and is concentric with the annular row of ratchet teeth 39. A gripping flange 41 is formed on the distal end 43 of the arbor 25.

The ratchet wheel 35 also has a second surface 45 opposite the first surface 37. A generally cylindrical spindle 47, which is oriented coaxially with the arbor 25, extends from the second surface 45. The spindle 47 has a plurality of longitudinal ridges 49 each having a generally triangular cross section, and a distal end 51 having a central receiver 53. An annular ridge 55 extends from the second surface 45 around the periphery of the ratchet wheel 35.

The floss cog 7 is adapted to hold a spool 57 of dental floss 59 which is press-fit onto the spindle 47 and held fast by the ridges 49. The dental floss 59 used with the device 1 is preferably manufactured of polytetrafluoroethylene, (also known as "PTFE"or "Teflon"® E. I. du Pont de Nemours and Company) because floss of this type is better able to resist the shredding which can result from the repeated use of a short section of floss which occurs when using a floss applicator equipped with ordinary floss.

In addition to the floss well 17, the cavity 15 of the handle portion 9 includes a floss channel 61 which extends from the floss guide 19 of the floss well 17 to the second end 14 of the handle portion 9, proximate the floss fork 13. The cavity 15 also includes a tool storage compartment 63 which is separated from the floss channel 61 by a dividing wall 65. The floss channel 61 and the storage compartment 63 share a floor 66 which slopes upwardly from bottom wall 21 of the floss well 17 toward the second end 14 of the handle portion 9. The tool storage compartment 63 may be used to contain dental hygiene tools such as a microbrush 67 and a pick 69 (FIG. 8) which are used to remove food particles and plaque from proximal spaces and orthodontics.

A hinge mount 71 having a pair of opposing receivers 73 is formed on the body 3 proximate the second end 14 of the handle portion 9. The lid 5 (FIGS. 6 and 7) has a pair of opposing posts 75 which engage the receivers 73 of the hinge mount 71 so that the lid 5 is pivotally attached to the body 3. The lid 5 is sized and shaped to cover the storage compartment 63, the floss channel 61 and the floss well 17. The lid 5 includes a latch 77 which selectively engages a tab 79 on the first end 12 of the handle portion 9. The lid 5 is molded of a strong, durable plastic, such as polycarbonate, which is preferably transparent so that a user of the device 1 can see how much floss 59 remains on the spool 57. The transparent lid 5 also allows the user to see the tools 67, 69 in the storage compartment 63.

The inside portion of the lid 5 which covers the floss well 17 includes a stub axle 81 which rotatably engages the receiver 53 of the floss cog 7 when the lid 5 is closed. The lid 5 serves to retain the floss cog 7 in position and to press the ratchet wheel 35 against the pawl 27, causing the tooth 29 to engage the teeth 39. The lid 5 also includes an annular ridge 83 centered about the stub axle 81 and having the same diameter as the annular ridge 55 of the floss cog 7. The annular ridges 55 and 83 serve as guides for the floss 59 and prevent it from sliding off the ends of the spool 57.

A floss guide 85 connected to the lid 5 is received in close parallel relation to the floss guide 19 of the floss well 17 upon closing of the lid 5. A hole or floss outlet 87 is provided in the lid 5 proximate the post 75 of the hinge mount 71 nearest the end of the floss channel 61.

The portion of the lid 5 which covers the tool storage compartment 63 may include a plurality of tool retaining tabs 88 designed to secure the pick 69 or any other suitable tool to the underside of the lid 5.

The floss fork 13 includes a pair of prongs 89 which extend outwardly from the second end 14 of the handle portion 9 and curve downwardly so that the tips 91 of the prongs 89 lie in spaced relation to one another along a line which is perpendicular to the longitudinal centerline of the body 3 and generally level with the outer surface of the bottom wall 21 of the floss well 17. The prongs 89 are separated by a gap 92 across which the floss 59 is stretched during use of the floss fork 13. Each prong 89 has a groove or floss track 93 which runs along the upper surface of the prong 89 from a point proximate the hinge mount 71 to the tip 91. Each tip 91 includes a post 95 which extends downwardly therefrom. A curved groove or channel 97 is formed in each of the tips 91 around the base of the post 95, running from the end of the floss track 93 to a point on the inner surface of the prong 89 behind the post 95.

A tie-off post 99 extends upwardly from the body 3 proximate the receiver 73 of the hinge mount 71 on the opposite side of the device 1 from the floss outlet 87. The same side of the body 3 includes a pair of tie-off hooks 101 which form a cleat for tying off the floss 59 and a metal floss cutter 103.

In order to route the floss 59 through the device 1, the spool 57 of floss 59 is first pressed onto the spindle 47 of the floss cog 7. The floss cog 7 is then installed in the floss well 17 with the arbor 25 through the receiver 23. The free end of the floss 59 is pulled through the outlet 87 of the lid 5 and the lid 5 is then closed. Closing the lid 5 leaves the floss 59 slidably captured between the floss guides 19, 85 proximate the floss well 17 and passing through the floss channel 61 to the outlet 87.

To complete the floss routing process, a length of floss 59 must be unwound from the spool 57, which requires the user to release the teeth 39 of the ratchet wheel 35 from the tooth 29 of the pawl 27, thereby allowing the floss cog 7 to rotate. This is accomplished by the user inserting a fingernail under the release tab 31, pressing against the gripping surface 33, and flexing the pawl 27 away from the ratchet wheel 35. Floss 59 is easily unwound from the spool 57 by pulling on the floss 59 while holding the release tab 31 as described.

When a sufficient length of floss 59 has been unwound from the spool 57, the user releases the release tab 31, letting the pawl 27 re-engage the ratchet wheel 35. The floss 59 is then routed through the floss track 93 of the prong 89 nearest the outlet 87, and around the post 95 of the same prong 89 with the floss 59 fitting into the channel 97. The floss 59 is then pulled across the gap 92 between the prongs 89 and around the post 95 of the second prong 89, through the channel 97, and up the floss track 93. The floss 59 is then threaded around the inside of the tie-off post 99 and wrapped around the tie-off hooks 101. It has been found that wrapping the floss 59 around the tie-off hooks 101 in a pattern of four figure-eights provides a tight connection between the floss 59 and the body 3 of the dental care device 1. Any excess floss 59 is cut off using the floss cutter 103. The floss is tightened by rotating the gripping flange 41 of the floss cog 7.

The tongue scraper 11 comprises a semicircular scraper blade 105 having a pair of opposed edges 107, the blade 105 being attached to the first end 12 of the handle portion 9 by a pair of outwardly curving mounting arms 109. The edges 107 of the tongue scraper blade 105 are formed so that one of the edges 107 is sharper than the other, thereby providing both fine and very fine scraping surfaces.

It is to be understood that while certain forms of the present invention have been illustrated and described herein, it is not to be limited to the specific forms or arrangement of parts described and shown.

What is claimed and desired to be secured by Letters Patent is as follows:

1. A dental care device for dispensing dental floss from a spool and holding a length of the floss under tension, said device including:
    a) a handle portion having first and second ends;
    b) a tongue scraper connected to said first end of said handle portion and having a blade with first and second edges, said first edge being sharper than said second edge;
    c) a floss fork connected to said second end of said handle portion and including first and second prongs extending outwardly from said handle portion, each of said prongs having a respective tip, said tips being separated by a gap, said prongs being adapted to support a length of dental floss across said gap; and
    d) a floss tensioner mounted in said handle portion and adapted to support a spool of dental floss and supply tension to the length of floss supported across said floss fork prongs.

2. The dental care device of claim 1, further including a tool storage compartment in said handle portion selectively enclosed by a lid hingedly connected to said handle portion.

3. A dental care device for dispensing dental floss from a spool and holding a length of the floss under tension, said device comprising:
    a) a body including:
        i) a handle portion having first and second ends and including a cavity having a bottom wall and upstanding sidewalls;
        ii) a tongue scraper connected to said first end of said handle portion, said tongue scraper including a blade with first and second edges, said first edge being sharper than said second edge; and
        iii) a floss fork connected to said second end of said handle portion and including first and second prongs extending outwardly from said handle portion, each of said prongs having a respective tip, said tips being separated by a gap, said prongs being adapted to support a length of dental floss across said gap;
    b) a lid having an inner surface and being hingedly connected to said handle portion and selectively covering said cavity; and
    c) a floss tensioner including:
        i) a floss cog mounted in said cavity and rotatably connected to said lid inner surface and said cavity bottom wall, said floss cog having a ratchet wheel with a plurality of teeth and a spindle connected to said ratchet wheel, said spindle being adapted to retain a spool of dental floss; and
        ii) a ratchet pawl connected to said body and selectively engaging said ratchet wheel teeth.

4. The dental care device of claim 3, wherein said body is constructed of polycarbonate.

5. The dental care device of claim 3, wherein said floss cog is constructed of nylon.

6. The dental care device of claim 3, wherein said lid is constructed of polycarbonate.

7. The dental care device of claim 3, wherein said lid is transparent.

8. The dental care device of claim 3, wherein said cavity includes a storage compartment for dental hygiene tools.

9. A dental care device for dispensing dental floss from a spool and holding a length of the floss under tension, said device comprising:
- a) a body including:
  - i) a handle portion having first and second ends and including a generally cylindrical floss well proximate said first end, said floss well having a bottom wall, a curved sidewall, and a floss guide connected to said sidewall, said bottom wall including a central receiver passing therethrough and an integral ratchet pawl oriented tangentially to said receiver and having a tooth projecting into said floss well and a release tab extending outwardly from said handle portion, said handle portion further including a floss channel extending from said floss guide to said second end of said handle portion and a tool storage compartment oriented between said floss well and said second end of said handle portion and at least partially separated from said floss guide by a dividing wall;
  - ii) a tongue scraper having a semicircular blade with first and second ends and first and second edges, said ends being connected to said first end of said handle portion by a pair of mounting arms; and
  - iii) a floss fork connected to said second end of said handle portion and including first and second prongs extending outwardly from said handle portion, each of said prongs having a respective tip, said tips being separated by a gap, said prongs being adapted to support a length of dental floss across said gap;
- b) a floss cog selectively rotatably mounted in said floss well, said cog including:
  - i) a ratchet wheel having first and second planar surfaces, said first surface including an annular row of ratchet teeth, said ratchet teeth selectively engaging said ratchet pawl tooth;
  - ii) a cylindrical arbor extending from said first surface of said ratchet wheel and through said floss well bottom wall central receiver, said arbor being concentric with said row of ratchet teeth and having a distal end with a gripping flange connected thereto; and
  - iii) a spindle extending from said second surface of said ratchet wheel, said spindle being oriented coaxially with said arbor and having a plurality of longitudinal ridges and a distal end with a central receiver, said spindle adapted to retain a spool of dental floss;
- c) a lid hingedly connected to said handle portion proximate said second end thereof, said lid selectively covering said floss well, said floss channel, and said tool storage compartment, said lid having:
  - i) a latch for selectively retaining said lid in a closed position;
  - ii) an inner surface;
  - iii) a stub axle connected to said inner surface and rotatably engaging said central receiver of said floss cog spindle when said lid is in the closed position; and
  - iv) a floss outlet extending through said lid proximate said first floss fork prong and aligned with said floss channel; and
- d) a cleat connected to said body proximate said second floss fork prong for tying off a free end of a length of dental floss.

10. The dental care device of claim 9, wherein said body is constructed of polycarbonate.

11. The dental care device of claim 9, wherein said floss cog is constructed of nylon.

12. The dental care device of claim 9, wherein said lid is constructed of polycarbonate.

13. The dental care device of claim 9, wherein said lid is transparent.

14. The dental care device of claim 9, wherein said floss fork prongs each include a floss track running from a point proximate said second end of said handle portion to said respective tip, and each said tip includes a post extending therefrom and a channel running from said floss track around said post to said gap.

15. A dental care device for dispensing dental floss from a spool and holding a length of the floss under tension, said device comprising:
- a) a body including:
  - i) a handle portion having first and second ends and including a generally cylindrical floss well proximate said first end, said floss well having a bottom wall, a curved sidewall, and a floss guide connected to said sidewall, said bottom wall including a central receiver passing therethrough and an integral ratchet pawl oriented tangentially to said receiver and having a tooth projecting into said floss well and a release tab extending outwardly from said handle portion, said handle portion further including a floss channel extending from said floss guide to said second end of said handle portion and a tool storage compartment oriented between said floss well and said second end of said handle portion and at least partially separated from said floss guide by a dividing wall;
  - ii) a tongue scraper having a semicircular blade with first and second ends and first and second edges, said ends being connected to said first end of said handle portion by a pair of mounting arms, said first edge of said blade being sharper than said second edge; and
  - iii) a floss fork connected to said second end of said handle portion and including first and second prongs extending outwardly from said handle portion, each of said prongs having a respective tip, said tips being separated by a gap, said prongs being adapted to support a length of dental floss across said gap;
- b) a floss cog selectively rotatably mounted in said floss well, said cog including:
  - i) a ratchet wheel having first and second planar surfaces, said first surface including an annular row of ratchet teeth, said ratchet teeth selectively engaging said ratchet pawl tooth;
  - ii) a cylindrical arbor extending from said first surface of said ratchet wheel and through said floss well bottom wall central receiver, said arbor being concentric with said row of ratchet teeth and having a distal end with a gripping flange connected thereto; and
  - iii) a spindle extending from said second surface of said ratchet wheel, said spindle being oriented coaxially with said arbor and having a plurality of longitudinal ridges and a distal end with a central receiver, said spindle adapted to retain a spool of dental floss;
- c) a lid hingedly connected to said handle portion proximate said second end thereof, said lid selectively covering said floss well, said floss channel, and said tool storage compartment, said lid having:
  - i) a latch for selectively retaining said lid in a closed position;
  - ii) an inner surface;

iii) a stub axle connected to said inner surface and rotatably engaging said central receiver of said floss cog spindle when said lid is in the closed position; and iv) a floss outlet extending through said lid proximate said first floss fork prong and aligned with said floss channel; and d) a cleat connected to said body proximate said second floss fork prong for tying off a free end of a length of dental floss.

16. A dental care device comprising:

a) a handle portion having first and second ends and including a cavity having a bottom wall and upstanding sidewalls;

b) a tongue scraper connected to said first end of said handle portion and having a blade with first and second edges, said first edge being sharper than said second edge;

c) a lid having an inner surface and being hingedly connected to said handle portion and selectively covering said cavity;

d) a floss tensioner including:
   i) a floss cog mounted in said cavity and rotatably connected to said lid inner surface and said cavity bottom wall, said floss cog having a ratchet wheel with a plurality of teeth and a spindle connected to said ratchet wheel; and
   ii) a ratchet pawl connected to said body and selectively engaging said ratchet wheel teeth;

e) a spool of dental floss, said spool being mounted on said floss cog spindle with a length of said floss extending therefrom; and f) a floss fork connected to said second end of said handle portion and including first and second prongs extending outwardly from said handle portion, each of said prongs having a respective tip, said tips being separated by a gap, said prongs being adapted to support the length of dental floss across said gap.

17. The dental care device of claim 16, wherein said cavity includes a storage compartment for dental hygiene tools.

18. The dental care device of claim 16, wherein said floss is manufactured of polytetrafluoroethylene.

19. A dental care device for dispensing dental floss from a spool and holding a length of the floss under tension, said device including:

a) a handle portion having first and second ends, said handle portion being ergonomically shaped so as to fit comfortably in the hand of a user with either said first end or said second end directed toward the user's mouth;

b) a tongue scraper connected to said first end of said handle portion;

c) a floss fork connected to said second end of said handle portion and including first and second prongs extending outwardly from said handle portion, each of said prongs having a respective tip, said tips being separated by a gap, said prongs being adapted to support a length of dental floss across said gap; and d) a floss tensioner mounted in said handle portion and adapted to support a spool of dental floss and supply tension to the length of floss supported across said floss fork prongs.

20. A dental care device comprising:

a) a handle portion having first and second ends and including a cavity having a bottom wall and upstanding sidewalls;

b) a floss fork connected to said second end of said handle portion and including first and second prongs extending outwardly from said handle portion, each of said prongs having a respective tip, said tips being separated by a gap, said prongs being adapted to support a length of dental floss across said gap a tongue scraper connected to said first end of said handle portion;

c) a floss tensioner including:
   i) a floss cog mounted in said cavity, said floss cog having a ratchet wheel with a plurality of teeth and a spindle connected to said ratchet wheel; and
   ii) a ratchet pawl connected to said body and selectively engaging said ratchet wheel teeth;

d) a spool of dental floss mounted on said floss cog spindle, a length of said dental floss being extendable from said spool to said floss fork and supportable across said gap; and e) a lid hingedly connected to said handle portion and selectively covering said cavity, said lid being transparent such that a user can view the amount of said dental floss remaining on said spool.

21. The dental care device of claim 20, wherein said cavity includes a storage compartment for dental hygiene tools other than said spool of dental floss.

22. The dental care device of claim 20, and further including a tongue scraper connected to said first end of said handle portion.

23. The dental care device of claim 22, wherein said tongue scraper includes a blade with first and second edges.

24. The dental care device of claim 23, wherein said first edge is sharper than said second edge.

25. The dental care device of claim 22, wherein said handle portion is ergonomically shaped so as to fit comfortably in the hand of a user with either said floss fork or said tongue scraper directed toward the user's mouth.

* * * * *